United States Patent
Forstreuter et al.

(10) Patent No.: US 9,108,003 B2
(45) Date of Patent: Aug. 18, 2015

(54) DRUG DELIVERY DEVICE

(75) Inventors: Axel Forstreuter, Frankfurt am Main (DE); Axel Teucher, Frankfurt am Main (DE)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 207 days.

(21) Appl. No.: 13/500,414

(22) PCT Filed: Oct. 14, 2010

(86) PCT No.: PCT/EP2010/065443
§ 371 (c)(1),
(2), (4) Date: Sep. 12, 2012

(87) PCT Pub. No.: WO2011/045385
PCT Pub. Date: Apr. 21, 2011

(65) Prior Publication Data
US 2012/0325865 A1    Dec. 27, 2012

(30) Foreign Application Priority Data

Oct. 16, 2009 (EP) .................................... 09173298

(51) Int. Cl.
*B65D 83/76* (2006.01)
*A61M 5/315* (2006.01)

(52) U.S. Cl.
CPC ....... *A61M 5/31558* (2013.01); *A61M 5/31553* (2013.01); *A61M 5/31585* (2013.01); *A61M 5/31536* (2013.01); *A61M 2005/3152* (2013.01); *Y10T 74/18576* (2015.01)

(58) Field of Classification Search
CPC .............. B65D 83/0011; A45D 40/04; A61M 5/31551; A61M 5/3155; A61M 5/31553; A61M 5/31585; A61M 5/31558; A61M 2005/3152; Y10T 74/18624

USPC .............. 222/389, 386, 386.5, 390, 282, 309; 74/89.23; 604/187, 218, 232, 207–211
See application file for complete search history.

(56) References Cited

U.S. PATENT DOCUMENTS 5,505,704 A      4/1996   Pawelka et al.
8,663,167 B2 *   3/2014   Bartha ......................... 604/154
(Continued)

FOREIGN PATENT DOCUMENTS

WO      99/38554       8/1999
WO      2004/078239    9/2004
(Continued)

OTHER PUBLICATIONS

European Search Report for European App. No. 09173298, completed Apr. 6, 2010.
(Continued)

*Primary Examiner* — Kevin P Shaver
*Assistant Examiner* — Robert Nichols, II
(74) *Attorney, Agent, or Firm* — McDonnell Boehnen Hulbert & Berghoff LLP (57) ABSTRACT

A drive mechanism for a drug delivery device is presented having a housing, an axially displaceable piston rod to act on a piston of a cartridge containing a medicinal product to be dispensed, a drive member threadedly engaged with the piston rod and being slidably disposed relative to the housing between a distal stop position and a proximal stop position. During the setting of a dose the drive member is rotatable with respect to the housing and a dose dial member is operably engaged with the drive member by means of a reduction gear, wherein the drive member at its proximal end section comprises a radially extending receptacle adapted to receive the reduction gear.

18 Claims, 7 Drawing Sheets

(56) References Cited

U.S. PATENT DOCUMENTS

| | | |
|---|---|---|
| 2002/0111587 A1 | 8/2002 | Hommann et al. |
| 2005/0004529 A1 | 1/2005 | Veasey et al. |
| 2005/0154347 A1* | 7/2005 | Neracher .................. 604/68 |
| 2006/0116647 A1 | 6/2006 | Geiser et al. |
| 2007/0093761 A1* | 4/2007 | Veasey et al. .............. 604/207 |
| 2007/0225657 A1 | 9/2007 | Hommann |
| 2008/0033369 A1* | 2/2008 | Kohlbrenner et al. ........ 604/207 |
| 2008/0051712 A1 | 2/2008 | Fiechter |
| 2011/0004166 A1* | 1/2011 | Wittmann et al. ........... 604/207 |

FOREIGN PATENT DOCUMENTS

| | | |
|---|---|---|
| WO | 2004/089450 | 10/2004 |
| WO | 2008/119691 | 10/2008 |
| WO | 2009/039851 | 4/2009 |

OTHER PUBLICATIONS

International Search Report for International App. No. PCT/EP2010/065443, completed Feb. 4, 2011.

International Preliminary Report on Patentability for International App. No. PCT/EP2010/065443, completed Feb. 21, 2012.

* cited by examiner

DRUG DELIVERY DEVICE

CROSS REFERENCE TO RELATED APPLICATIONS

The present application is a U.S. National Phase Application pursuant to 35 U.S.C. §371 of International Application No. PCT/EP2010/065443 filed Oct. 14, 2010, which claims priority to European Patent Application No. 09173298.2 filed on Oct. 16, 2009. The entire disclosure contents of these applications are herewith incorporated by reference into the present application.

FIELD OF THE INVENTION

The present invention relates to a drug delivery device such as a pen-type injector and to a corresponding drive mechanism, wherein a single or a number of pre-set doses of a medicinal product can be administered. In particular, the present invention relates to drive mechanisms and drug delivery devices, where a user may set the dose.

BACKGROUND

User operated drug delivery devices are as such known in the prior art. They are typically applicable in circumstances, in which persons without formal medical training, i.e., patients, need to administer an accurate and predefined dose of a medicinal product, such as heparin or insulin. In particular, such devices have application, where a medicinal product is administered on a regular or irregular basis over a short term or long-term period.

In order to accommodate with these demands, such devices have to fulfil a number of requirements. First of all, the device must be robust in construction, yet easy to use in terms of handling and in understanding by the user of its operation and the delivery of the required dose or medicament. The dose setting must be easy and unambiguous. Where the device is to be disposable rather than reusable, the device should be inexpensive to manufacture and easy to dispose. Moreover, the device should be suitable for recycling. To meet these requirements, the number of parts required to assemble the device and the number of material types the device is made from need to be kept to a minimum.

Document US 2005/0004529 A1 for instance discloses a drive mechanism for use in a drug delivery device comprising an epicyclic gear box. This drive mechanism further has a piston rod of non-circular cross-section, a dose dial sleeve threadedly engaged with a housing and a drive sleeve located between the housing and the piston rod. Further, the dose dial sleeve is releasably connected to the drive sleeve by the epicyclic gear box. For setting of a desired dose to be delivered, a user rotates a second part of the dose dial sleeve. During such a dose setting, the dose dial sleeve, the drive sleeve and the sun gear of the epicyclic gear box are coupled together and the planetary gear cannot rotate. Also, when the dose dial sleeve is rotated, the piston rod remains in contact with a second, proximal face of cartridge's piston.

For dispensing of a selected dose, a user depresses the dose button. Displacing the dose button towards a first end of the device couples the dose button to the sun gear to lock the sun gear in rotation to the dose button. Further, a shoulder on the sun gear locking a clutch means between the drive sleeve and the dose dial sleeve is disengaged, thereby allowing the drive sleeve to rotate with respect to the dose dial sleeve. During dose dispensing, the planetary gear then creates a gear ratio between the sun gear and the dose dial sleeve.

Such known drive mechanism requires a clutch mechanism for a releasable connection of dose dial sleeve and drive sleeve by an epicyclic gear box. However, setting of particularly small doses as well as dispensing an amount of the medicinal product smaller than a standard dose unit is almost not possible.

Particularly in the field of paediatrics, there is a need of administering particularly small doses of a medicinal product.

It is therefore an object of the present invention, to provide a drive mechanism and a drug delivery device adapted to dispense a particularly small dose or multiple small doses of a medicinal product. The drive mechanism should be easy and intuitive in handling and should provide an accurate and fine-tuned dose setting. It is further an object of the invention, to provide a drive mechanism and a drug delivery device comprising a simple internal structure, which is inexpensive to produce as well as fast and easy to assemble. Additionally, the drug delivery device and its dose dispensing mechanism should be mechanically stable and robust.

SUMMARY

The present invention provides a drive mechanism for a drug delivery device for dispensing of at least one dose of a medicinal product. The mechanism comprises a housing and an axially displaceable piston rod, adapted to act on a piston of a cartridge. The cartridge comprises the medicinal product to be dispensed by the drive mechanism.

Depending on the purpose of the drive mechanism, a distal outlet of the cartridge may be engaged with a needle, a cannula, an infusion tube or with a similar delivery device. The cartridge, which is to be disposed in the housing may be designed as replaceable or disposable ampoule, carpule or syringe or as a similar medicinal product-containing container. The cartridge's piston is displaceable in distal direction for expelling of a pre-defined dose of medicinal product from the cartridge. The piston's distal and dose expelling motion is typically governed by a corresponding distally directed motion of the piston rod, which typically abuts the proximal end face of the cartridge's piston by means of a pressure piece axially secured to the piston rod's distal end.

The drive mechanism further comprises a drive member threadedly engaged with the piston rod, wherein the drive member is slidably disposed relative to the housing between a distal stop position and a proximal stop position. This axial displacement of the drive member is typically of non-rotating type. Accordingly, the drive member is typically rotatably locked with respect to the housing during axial displacement.

For setting of a dose, the drive member is rotatable with respect to the housing. By means of the threaded engagement with the piston rod, a rotation of the drive member preferably induces a distally directed displacement of the piston rod. For this purpose, the drive member is at least rotatably mounted with respect to the housing. Preferably, with the drive member in its proximal stop position, the piston rod, in particular its pressure piece does not abut the proximal end face of the cartridge's piston. Hence, a distally directed dose setting displacement of the piston rod is conductible in a configuration of the drive mechanism, in which the drive member is in its proximal stop position and in which the piston rod and the piston are spatially separated from each other.

However, the drive member does not necessarily have to be in proximal stop position in order to be rotated. It is conceivable, that the drive member is axially displaced from a distal to a proximal stop position in the course of a dose setting rotational motion, which is typically induced by a user.

The drive mechanism according to the present invention further comprises a dose dial member, which is operably engaged with the drive member by means of a reduction gear, preferably by means of a mechanic reduction gear. A rotative movement of the dose dial member therefore creates a gear ratio, such that the drive member rotates at a lower rate of rotation compared to the rate of rotation of the dose dial member. By means of the reduction gear, a precise and fine-tune rotational movement of the drive member and a correspondingly precise axial displacement of the piston rod can be achieved, which allows for a sufficiently fine-tuned setting of a dose to be dispensed in a subsequent dose dispensing procedure. In this way, particularly small doses comprising a rather small amount of the medicinal product, even smaller than a standard dose unit can be precisely set and dispensed.

The drive member at its proximal end section comprises a receptacle adapted to receive the reduction gear. Preferably, said receptacle radially extends with respect to a shaft portion of the drive member and may therefore radially protrude from a proximal end section of the housing. By arranging the reduction gear in said receptacle, a rather compact and space-saving design of the drive mechanism can be attained. Moreover, the dose dial member can be connected to the drive member by way of the reduction gear being rigidly attached thereto. Dose dial member, reduction gear and drive member may therefore provide a pre-assembled drive unit which is to be coupled with the piston rod. In this way, even existing drug delivery devices and device designs may be equipped and/or upgraded with the reduction gear mechanism by simply interchanging a conventional drive member by said drive unit.

Additionally, since setting of a dose is to be conducted with the drive member in its proximal stop position, a resulting dose-setting axial displacement of the piston rod is smooth-running due to the preferred axial gap between piston and piston rod in the dose setting configuration of the drive mechanism.

The present invention therefore provides a precise, fine-tuned and smooth setting of doses comprising a comparatively small amount of the medicinal product, which may be particularly applicable for paediatric purposes.

According to a further embodiment of the invention, the drive member is slidably disposed relative to the housing from the proximal stop position to the distal stop position for dispensing of a dose. This dose-dispensing axial displacement of the drive member is typically accompanied by a corresponding axial displacement of the piston rod in distal direction. The mechanical coupling and mutual engagement of drive member and piston rod can be such, that an axial displacement of the drive member is transferred to the piston rod in a direct or indirect way. It is conceivable, that a distally directed displacement of the piston rod matches the corresponding distal displacement of the drive member. Alternatively, it is conceivable, that the mechanical coupling of piston rod and drive member inherently comprises a reduction mechanism.

In typical embodiments, during dose dispensing, the drive member is rotatably fixed with respect to the housing and is only axially displaceable within the housing. Due to such rotational locking of drive member and housing, the reduction gear is principally deactivated since dose dial member and drive member are permanently mutually engaged by means of the reduction gear. Due to this permanent engagement, a rotational blocking of either one of the components, dose dial member or drive member therefore leads to a corresponding rotative blocking of the respective other component, drive member or dose dial member.

For setting of a dose, the drive member is rotatably released. Even though not principally required it might be of advantage, if the drive member and/or the dose dial member are axially locked but rotatably released in a dose setting configuration of the drive mechanism.

A thrust required for axially displacing the piston rod in distal direction may be provided by the user itself by depressing of the dose dial member and/or the drive member in distal direction. Such a user-induced or user-supported distal displacement of the drive member slaves the piston rod in distal direction for dispensing of the previously set dose.

According to a further embodiment of the invention, the housing comprises a through opening for guiding the piston rod. This through opening is preferably designed for guiding of a distal portion of the piston rod. Hence, said through opening is arranged in a distal section of the housing. It may serve as an axial conduct or guidance and keeps the piston rod radially in place. The usable clearance of the through opening may directly correspond to the diameter of the piston rod. Also, the through opening may adapt to the piston rod's cross-sectional geometry.

In a further preferred embodiment of the invention, said through opening of the housing and the distal portion of the piston rod are correspondingly threaded. In this way, piston rod and housing are threadedly engaged by means of said through opening, typically comprising an inner thread matching with an outer thread of the piston rod. In this way, axial displacement of the piston rod, either in distal or proximal direction is accompanied by a respective relative rotation of piston rod and housing, wherein the rate of rotation is governed by the lead of the piston rod's thread.

According to another embodiment of the invention, the drive member comprises a drive sleeve, which is adapted to receive the piston rod at least partially. Further, the piston rod comprises a proximal portion with an outer proximal thread matching with an inner thread of the drive sleeve. Typically, the drive sleeve at least partially extends about the piston rod in axial direction. By means of the threaded engagement of drive sleeve and piston rod, a rotative movement of the piston rod can be induced by means of displacing of the drive sleeve in axial or proximal direction without rotating the latter. Furthermore, since the piston rod is threadedly engaged with the housing, it is possible to slidingly displace the drive sleeve relative to the housing while drive sleeve and housing are rotationally interlocked. Since the piston rod is threadedly engaged with the drive sleeve as well as with the housing, it provides a mechanical coupling between drive sleeve and housing.

In a further aspect, the piston rod's distal thread and the piston rod's proximal thread are oppositely handed and comprise different leads. By providing the piston rod's proximal and distal end sections with oppositely handed threads, it can be achieved, that a relative axial displacement between drive sleeve and piston rod leads to a rotation of the piston rod relative to the drive sleeve. If the drive sleeve and the housing do not experience a relative rotation or only a reduced or oppositely directed relative rotation, the induced rotative movement of the piston rod may lead to an axial displacement of the piston rod relative to the housing. Due to the oppositely handed threads, the mechanical coupling of drive sleeve and piston rod results in equally directed axial displacements of piston rod and drive sleeve.

Since the distal thread and the proximal thread of the piston rod may further comprise different leads, the threaded engagement of piston rod, housing and drive sleeve may further provide a gear transmission ratio. If for instance the lead of the piston rod's proximal thread is larger than the lead of the piston rod's distal thread, an axial displacement of the piston rod induced by a corresponding axial displacement of the drive sleeve will be reduced or enlarged by a factor given by the ratio of distal and proximal thread.

In a further preferred embodiment, the threaded engagement of piston rod and drive member, in particular the threaded engagement of piston rod and drive sleeve, is of non-self-locking type. In this way, an axial but non-rotational displacement of the drive member and the drive sleeve relative to the housing results in a corresponding rotational movement of the piston rod, which in turn leads to a respective axial displacement of the piston rod as governed by the threaded engagement of the piston rod and the housing.

In a further aspect and according to another embodiment of the invention, the drive member is spring biased with respect to the housing in axial direction. Typically, a spring element is arranged between a proximal, flange-like or socket-like portion of the drive member and a respective shoulder of the housing. In this way, the drive member may be autonomously displaced from its distal stop position to its proximal stop position in order to transfer the drive mechanism in a dose setting configuration. The respective movement of the drive member in proximal direction may be conducted exclusively by the effect of a spring element. Alternatively, the spring element may act auxiliary, e.g. to support a user-conducted displacement.

Preferably, distal and proximal stop positions of the drive member are fixed relative to the housing. The axial distance between proximal and distal stop position determines the maximum distance, the piston rod may be displaced during a dose dispensing procedure. However, due to the two-fold threaded engagement of the piston rod with the housing and with the drive sleeve, the magnitude of axial displacement experienced by the piston rod during a displacement of the drive sleeve between proximal and distal stop position is governed by the gear transmission ratio as defined by the threaded engagement of the piston rod with the housing and with the drive sleeve.

In another preferred embodiment, the dose dial member and the drive member are permanently axially engaged, e.g. by means of the reduction gear. In this way, any axial displacement of the drive member between its proximal and distal stop position is accompanied by a respective axial displacement of the dose dial member.

According to another preferred embodiment, a proximally directed axial displacement of the drive member is delimited by a radially extending flange of the dose dial member. Said flange of the dose dial member is further adapted to abut with a radially inwardly directed flange-like stop of the housing. Typically, during a proximally directed axial displacement of drive member and dose dial member, the dose dial member at least partially extends beyond the proximal end face of the housing. If the proximal stop position of drive member and dose dial member is reached, the dose dial member is free to be rotated by a user for transmitting a respective rotational movement to the drive sleeve, which in dose setting configuration preferably remains axially fixed with respect to the housing. Due to the two-fold threaded engagement, the piston rod becomes subject of a combined rotational and axial displacement.

Such distally directed axial displacement of the piston rod during dosing setting diminishes an axial gap between the piston rod's pressure piece and the proximal end face of the piston. In a subsequent dose dispensing procedure, by depressing the dose dial button in distal direction, leading to a corresponding distal displacement of the drive member, the piston rod experiences a distally directed axial displacement, which induces a distal displacement of the cartridge's piston required for dispensing of the set dose. This way, the displacement of the piston during dose dispensing substantially equals the axial displacement experienced by the piston rod during a dose setting procedure.

By a complementary design and geometry of dose dial member and radially inwardly directed flange portion of the housing, the proximal stop position of the drive member can be precisely specified.

According to another preferred embodiment of the invention, the drive member or the drive sleeve is locked in the distal stop position with respect to the housing by means of a latch mechanism. The latch mechanism may comprise a spring-biased latch, which is either arranged at the housing or at the drive member. The latch or latch mechanism is adapted to axially interlock the drive member with respect to the housing. It is further of advantage, when a latch means of the drive member comprises a radial symmetry in order to provide axial locking of the drive member's sliding movement irrespective of its angular position or angular orientation.

In another preferred embodiment, the receptacle located at the proximal end of the drive member houses the reduction gear and is closed and/or covered in proximal direction by the dose dial member. The dose dial member is rotatably connected to the mechanic reduction gear and is therefore axially fixed thereto. Consequently, the dose dial member is rotationally supported with respect to the drive member and its housing. The reduction gear is preferably confined by the receptacle at least in distal and radial direction, while the dose dial button substantially extends across the lateral cross-section of the reduction gear, to serve as a proximal protection and/or housing means for the reduction gear.

In typical configurations, the reduction gear comprises an epicyclic gear or a harmonic drive. In this way, a rather large gear ratio and a correspondingly precise rotational adjustment of dose dial member and interconnected drive member can be achieved. Also, an epicyclic gear box can be realized in a cost- and space-efficient way. Additionally, the reduction gear might be entirely or at least partially implemented in plastic material, which helps to reduce the overall weight and production costs of the drive mechanism and in particular of its axially displaceable components.

According to a further preferred embodiment, the reduction gear comprises a number of planetary gears that mesh with a sun gear and with a surrounding ring gear. The sun gear is preferably rotatably locked with the dose dial member and the ring gear is rotatably locked with the drive member. In this way, a rotation of the dose dial member and the sun gear is transferred to a respective rotation of the drive member, wherein the diameter and the toothing of the respective gears determine the gear transmission ratio of dose dial member and drive member.

Further and according to another aspect of the invention, the dose dial member extends in proximal direction from a proximal end face of the housing when the drive member reaches its proximal stop position. Since the dose dial member at least partially protrudes from the proximal end face of the housing, it can be depressed in distal direction for dispensing of a dose. A user-controlled dose dispensing distal displacement of dose dial member, drive member and interconnected reduction gear is typically delimited by the latch mechanism. For a subsequent dose setting procedure, the latch mechanism is to be released, such that the drive member, the dose dial member and the reduction gear are displaced in proximal direction, e.g. under the effect or by means of the spring element.

According to a further aspect, the dose dial member, the reduction gear and/or the drive member are rigidly connected with each other in axial direction. Dose dial member, reduction gear and drive member may therefore provide a pre-assembled drive unit to become operably coupled with the piston rod. Moreover, an axial displacement of the dose dial button can be transferred unaltered to the drive member and vice versa. This way, the dose dial button may also serve as a thrust receiving element to transfer externally applied injection forces into a respective distally directed motion of the drive member, which may thus lead to a respective axial feed motion of the piston rod.

In another preferred embodiment, the dose dial member is therefore axially connected with the reduction gear and hence with drive member to displace the drive member in distal direction when a distally directed injection force acts onto the dose dial member. This way the dose dial member may provide a double function. By turning or twisting the dose dial member, a predefined dose can be set and subsequently, by exerting axially directed pressure onto the dose button, the drive mechanism, at least its drive member can be manually and precisely displaced in distal direction for expelling of a dose of the medicinal fluid contained in the cartridge.

In another independent aspect, the invention provides a drive mechanism for a drug delivery device comprising a housing and an axially displaceable piston rod, which is adapted to act on a piston of a cartridge to be placed inside said housing and containing a medicinal product to be dispensed. The drive mechanism further comprises a drive member which is threadedly engaged with the piston rod. The drive mechanism also comprises a dose dial member, which is operably engaged with the drive member by means of a reduction gear. Said reduction gear is exclusively operable and is exclusively designed to reduce a drive member's displacement during setting of a dose. Preferably, said coupling of dose dial member and drive member by means of a reduction gear is explicitly designed for a precise and fine-tuned dose setting displacement of the drive member.

Here, but also with all other described embodiments, the piston rod the drive member the dose dial member and/or the reduction gear are rotatably supported about a common or several axes of rotation being substantially co-aligned. Hence, the axes of rotation of the drive member, the dose dial member and/or the reduction gear substantially overlap in an axial projection. This way, a rather compact and space-saving design of the drive mechanism and the respective drug delivery device can be attained. In particular, the drive member and the dose dial member can be axially aligned in order to attain a rather compact design in radial direction, which allows to implement an injection device such like a compact pen-type injector.

During dose dispensing, the reduction gear is preferably inoperable or deactivated. However, a threaded engagement or mechanical coupling of dose dial member and drive member remains intact. Since during a typical dose dispensing procedure, neither drive member nor dose dial member experience a rotational displacement, the reduction gear provides an immediate and direct axial coupling of dose dial member and drive member. A releasable interconnection or coupling of dose dial member, reduction gear and drive member is therefore not required.

In another aspect, the invention further provides a dose dispensing device comprising a dose dispensing mechanism according to any one of the above described embodiments and various combinations thereof. Preferably, the dose dispensing device further comprises a cartridge filled with the medicinal product be dispensed. The device may be of reusable and/or disposable type. Preferably, the device is to be commercially distributed with a filled cartridge readily disposed therein and is further of disposable type. In this way, after consumption of the medicinal product, the entire device is intended to be discarded.

The term "medicament" or "medicinal product", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39), des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be apparent to those skilled in the art, that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

Without any limitation, the present invention will be explained in greater detail below in connection with preferred embodiments and with reference to the drawings in which.

DETAILED DESCRIPTION

Figure 1:
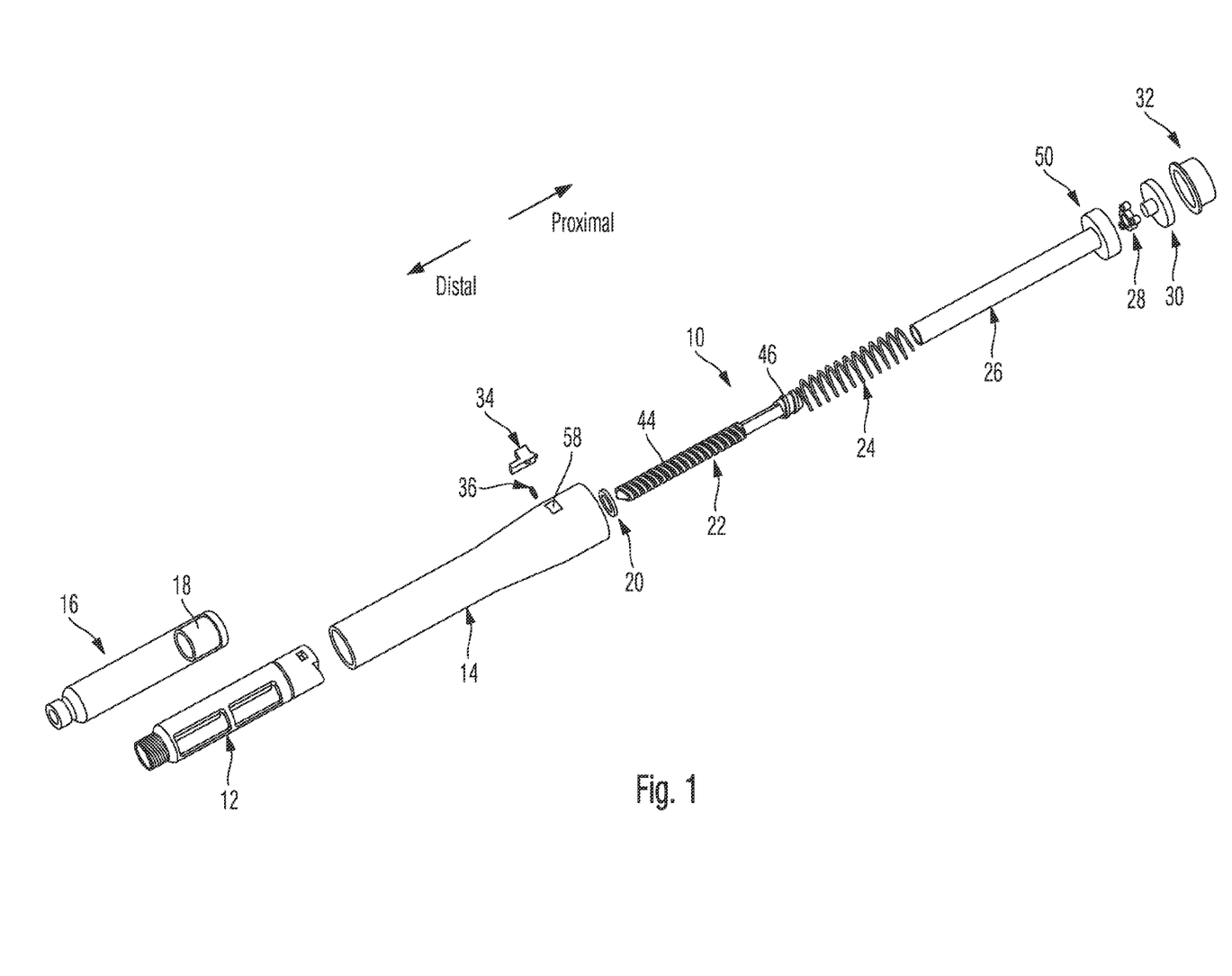
FIG. 1 schematically illustrates the various components of the drive mechanism in an exploded view.
Figure 3:
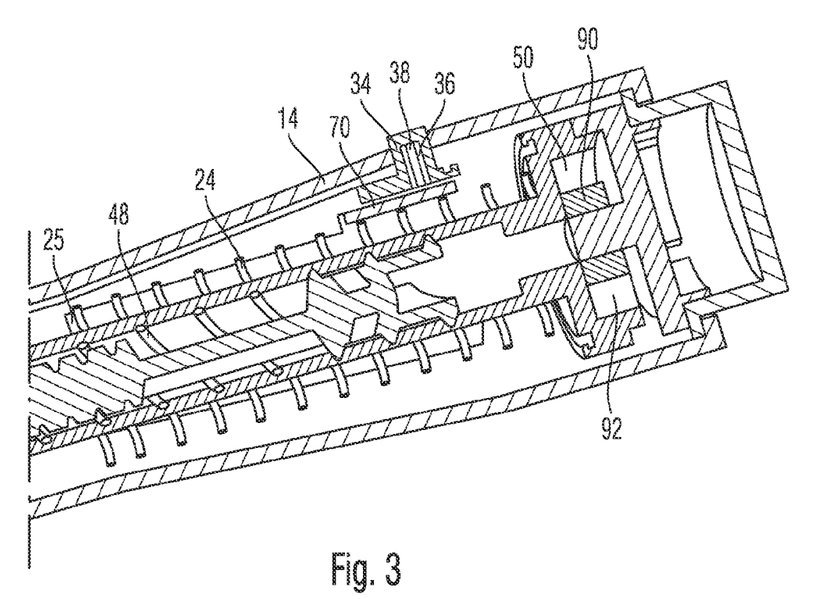
FIG. 3 illustrates the drive mechanism according to FIG. 2 with the drive member in its proximal stop position, FIG. 4 schematically illustrates a cartridge holder in a perspective illustration, FIG. 5 illustrated the housing in a perspective view.
Figure 4:
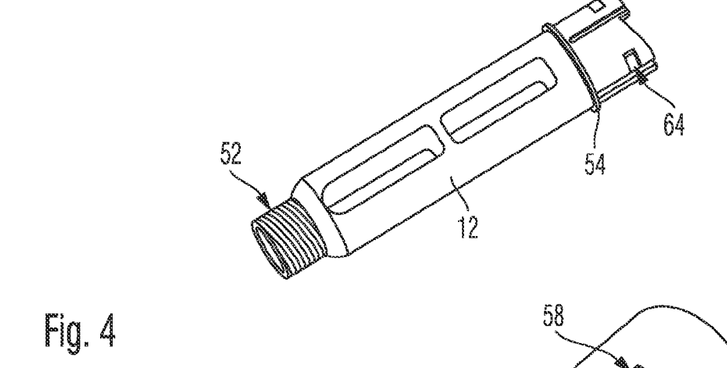
Figure 5:
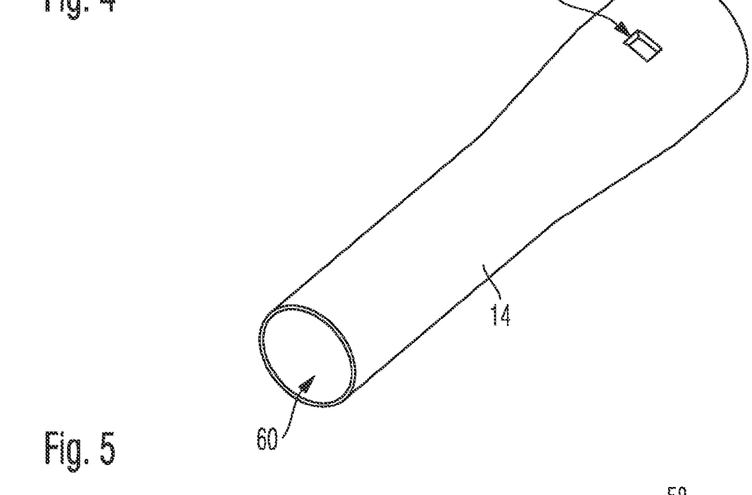

A drug delivery device of pen-injector type together with its drive mechanism 10 is illustrated in an exploded view in FIG. 1. The drive mechanism 10 comprises a housing 14 of substantially cylindrical shape. The housing 14 receives various mechanically interacting components of the drive mechanism 10 as further illustrated in FIGS. 2 and 3. At its distal end section, the housing 14 comprises a receptacle 60 as shown in FIG. 5. The receptacle 60 is adapted to receive a proximal portion of a cartridge holder 12 as illustrated in FIG. 4.

Figure 7:
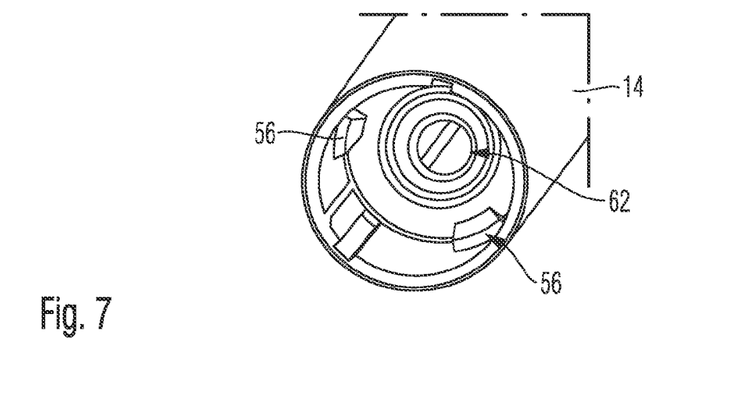

The cartridge holder 12 and the housing 14 are adapted to mutually engage by means of a positive locking. For this purpose, the cartridge holder 12 comprises numerous recesses 64 at its outer circumference of its proximal end section. Accordingly, the proximal section of the housing 14 comprises corresponding detent elements 56 as illustrated in FIG. 7. These detent elements 56 are adapted to fit into and to match with the recesses 64 of the cartridge holder 12. Further, the cartridge holder 12 comprises an annular collar 54, which serves as abutment for a distal end face of the housing's 14 receptacle 60.

The entire drug delivery device can be designed as disposable device, wherein after dispensing of a last dose, the entire device is intended to be disposed. The device could then be subject to a recycling process, in which for instance the drive mechanism 10 might be reused. Alternatively, e.g. by means of a releasable positive locking of cartridge holder 12 and housing 14, the drug delivery device could be subject to disassembling allowing for a replacement of an empty cartridge 16. In this way, the device may also be designed as reusable pen-type injector.

At its distal end, the cartridge holder 12 has a threaded socket 52, which is designed as a stepped down neck portion and which provides an inside abutment for a corresponding socket portion of the cartridge 16. At its outer circumference, the socket 52 comprises a thread, e.g. for mounting of an injection needle, a cannula or the like.

Figure 6:
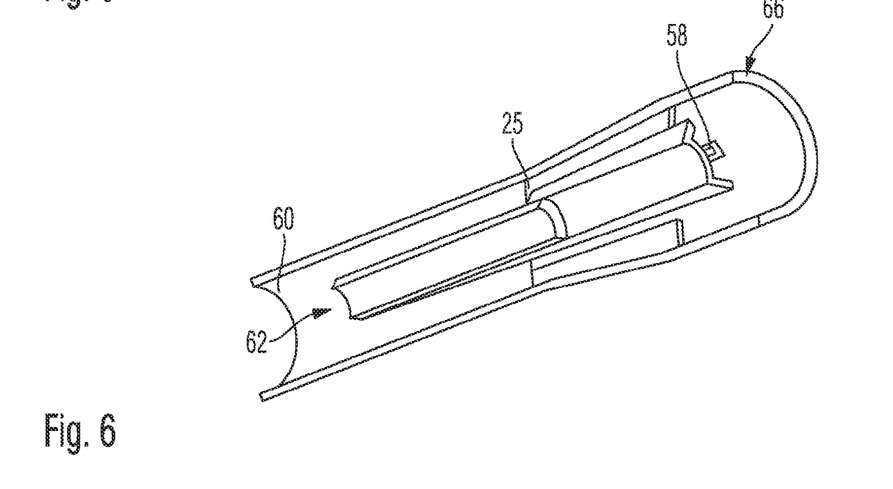
FIG. 6 shows a cross-sectional and perspective illustration of the housing, FIG. 7 perspectively illustrates the housing's distal portion, FIG. 8 perspectively illustrates the housing's proximal portion.
Figure 8:
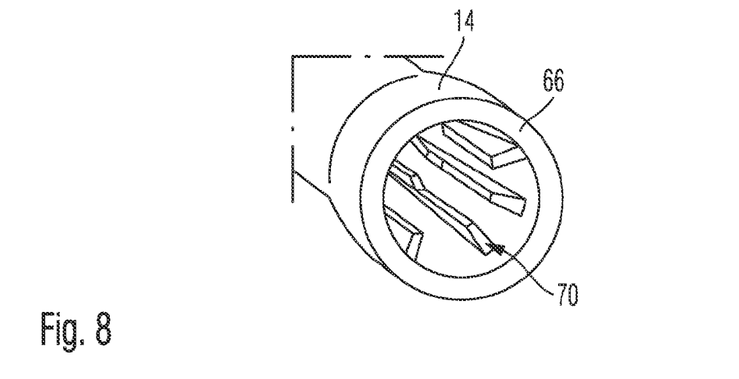
Figure 10:
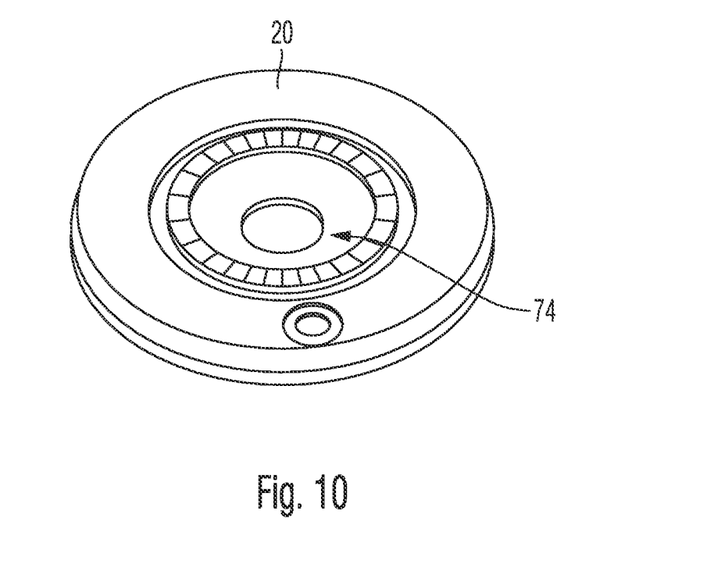
Figure 11:
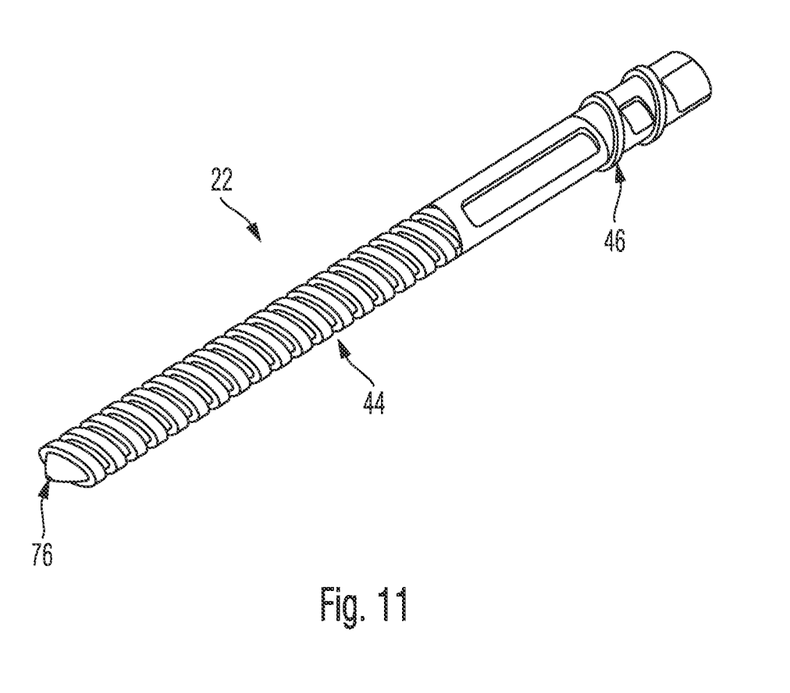
Figure 12:
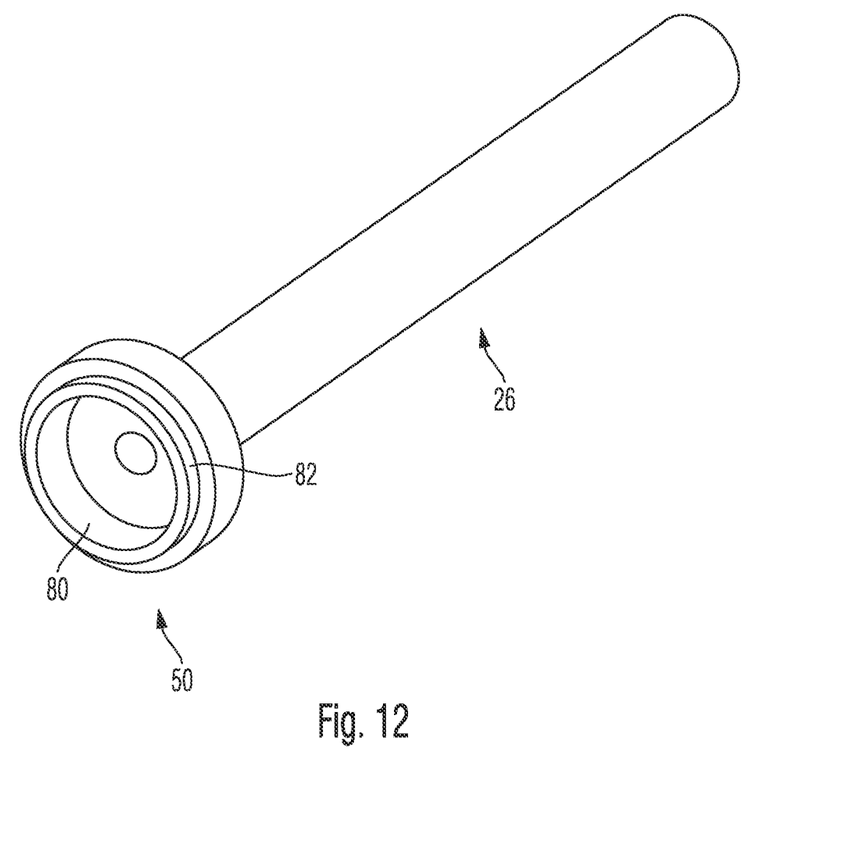
FIG. 12 shows the drive sleeve in a perspective illustration.

The housing, as illustrated in FIGS. 6 through 8 further comprises a circular through opening 62 near its distal receptacle 60. The through opening 62 of circular shape comprises an inner thread matching with the outer thread 44 of the piston rod 22, as illustrated in FIGS. 1 and 11. In this way, an axial relative displacement of piston rod 22 and housing 14 is always accompanied by a relative rotative displacement of housing 14 and piston rod 22. With its distal end 76, the piston rod 22 is adapted to be coupled with a pressure piece 20. The pressure or thrust piece 20 as illustrated in FIG. 10 comprises a respective through opening 74 adapted to receive the piston rod's 22 distal end 76.

Pressure piece 20 and piston rod 22 are preferably positively locked, wherein the pressure piece 20 remains free to rotate with respect to the piston rod's 22 long axis. The pressure piece 20 is further adapted to abut a proximal end face of the cartridge's 16 piston 18 and to transfer a required thrust to the piston 18 for the purpose of dispensing of a pre-defined dose of the medicinal product.

The piston rod 22 comprises a distal thread 44 engaged with the though opening 62 of the housing 14 and further comprises a proximal thread 46 engaged with a corresponding inner thread 48 of a drive sleeve 26 at least partially extending about the piston rod 22. Typically, proximal thread 46 and distal thread 44 are oppositely handed and comprise different leads. In preferred embodiments, the threaded engagement of the piston rod 22 and the drive sleeve 26 is of non-self-locking type. In this way, an axially directed displacement of the drive sleeve 26 leads to a respective rotation of the piston rod 22 and according to the threaded engagement of piston rod 22 and housing 14 to a respective relative axial displacement of piston rod 22 and housing 14.

Furthermore, the diameter of the piston rod's 22 proximal thread 46 is larger than the diameter of the distal thread 44. In this way, a mechanical interaction of drive sleeve 26 and distal thread 44 of the piston rod 22 can be precluded.

Since the proximal thread 46 and distal thread 44 of the piston rod 22 comprise different leads, the threaded engagement of housing 14, piston rod 22 and drive sleeve 26 inherently provides a gear transmission ratio. If for instance the drive sleeve 26 is subject to an axial but non-rotative displacement relative to the housing 14, the piston rod 22 will become subject to a respective distally directed displacement. This displacement of the piston rod 22 and the drive sleeve's 26 displacement differ in magnitude by the ratio of the leads of distal thread 44 and proximal thread 46.

Figure 2:
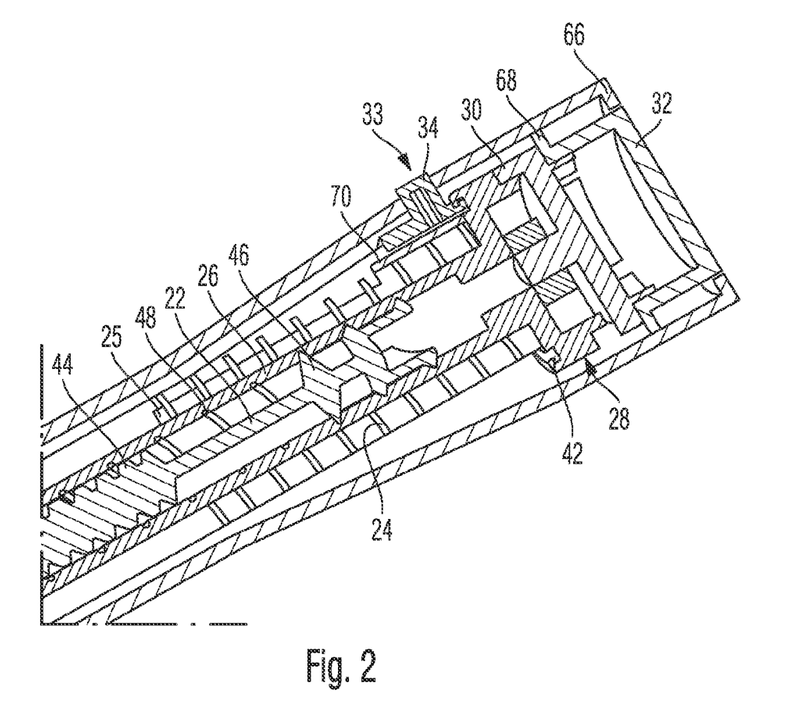
FIG. 2 illustrates the drive mechanism in cross-sectional view with the drive member in its distal stop position.

At its proximal end section, the housing 14 comprises a receptacle to receive the drive sleeve 26 and the piston rod 22. For axial and radial guidance of the drive sleeve 26, the housing 14 comprises numerous axial extending and radially inwardly protruding guiding ribs 70 as shown in FIG. 8. The drive sleeve as illustrated in FIG. 1 through 3 is spring-biased with respect to the housing 14 by means of a spring element 24. Said spring element abuts with a radially inwardly protruding shoulder 25 of the housing 14. In proximal direction, the spring element 24 abuts with a radially extending socket of a receptacle 50 formed at the drive sleeve's 26 proximal end section.

Figure 9:
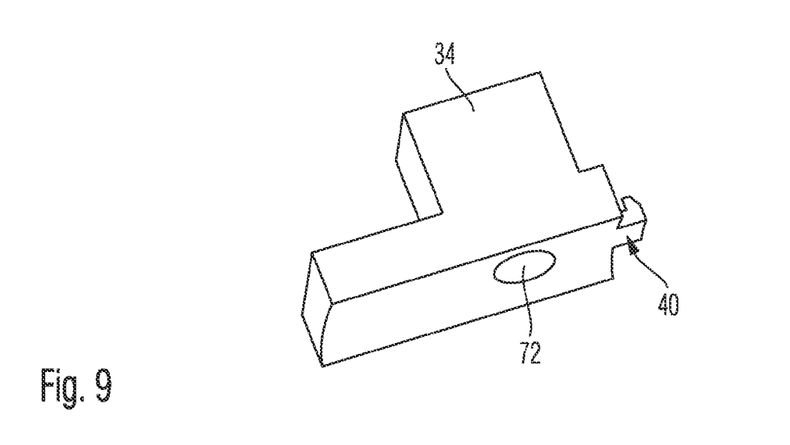
FIG. 9 illustrates a latch member in a perspective illustration, FIG. 10 perspectively depicts a pressure piece to be mounted to the piston rod's distal end, FIG. 11 perspectively shows the piston rod.

Under the effect of the spring element 24, the drive sleeve 26 can be autonomously displaced from the distal stop position as illustrated in FIG. 2 to the proximal stop position as illustrated in FIG. 3. In its distal stop position, the drive sleeve 26 is axially secured by means of an interlock member 34 of a latch mechanism 33. The interlock member 34 as illustrated in FIG. 9 comprises a receptacle 72 in order to receive a peg 38 arranged to or integrally formed with the housing 14. The receptacle 72 is further adapted to receive a spring element 36, which serves to bias the interlock member 34 in a radial outward direction.

At a proximal end section, the interlock member 34 comprises a hook-like latch 40, which is adapted to match and snap fit with an annular groove 42 provided at a radially extended socket of the drive sleeve's 26 receptacle 50. The interlock member 34 is further adapted to protrude from a recess 58 formed in the housing 14. In this way, by depressing the interlock member 34, the latch mechanism 33 can be released and the drive sleeve 26 can be axially displaced in proximal direction under the effect of the spring element 24.

Figure 14:
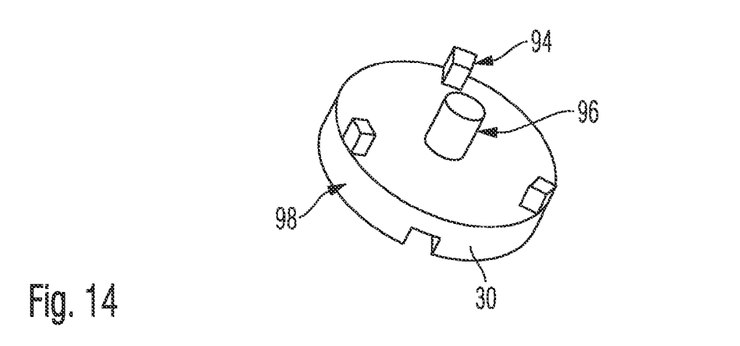
Figure 15:
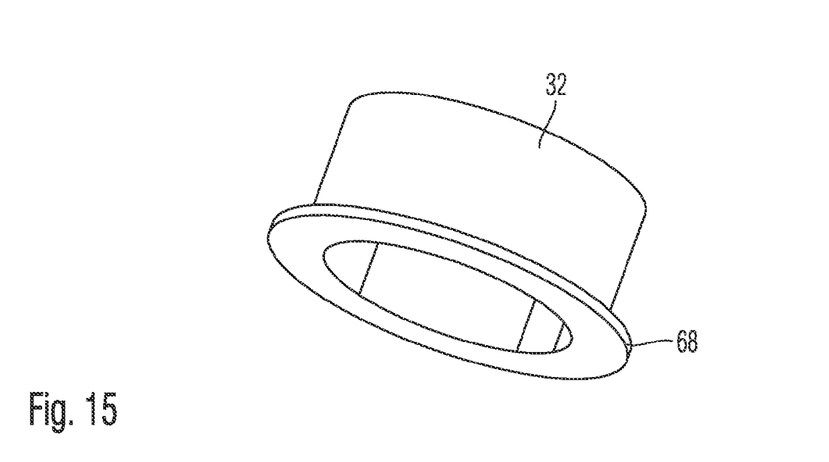
FIG. 15 in a perspective illustration depicts the dose dial button.

The proximal displacement of the drive sleeve 26 is delimited by an abutment of a radially inwardly protruding stop 66 of the housing 14 interacting with an annular and radially extending flange-like socket 68 of a dose dial button 32. The dose dial button 32 is permanently and rigidly fixed to a support member 30 as illustrated in FIG. 14. For this purpose, the support member 30 for instance comprises a circumferential thread 98 allowing to establish a screwed connection of support member 30 and dose dial button 32.

Figure 13:
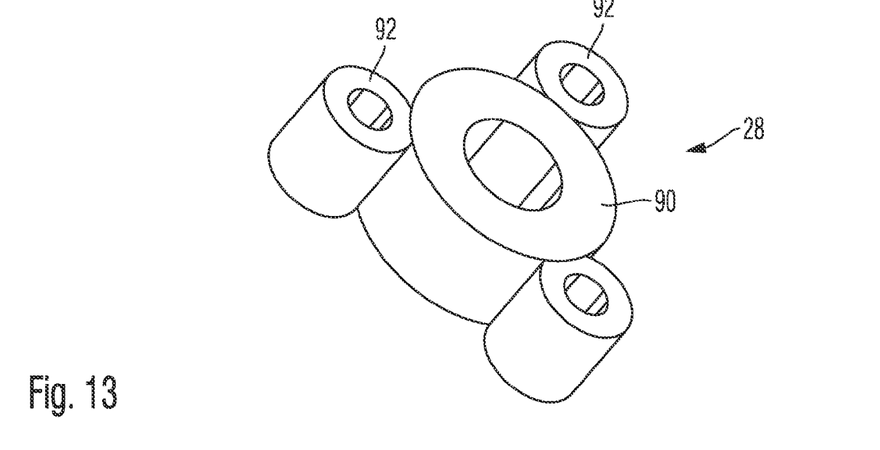
FIG. 13 illustrates sun gear and planetary gears of the epicyclic gear box, FIG. 14 in a perspective illustration shows a support member to be interconnected with the sun gear and the dose dial button.

The support member 30 further has an axially extending pin 96, which is adapted to receive a sun gear 90 of an epicyclic gear 28, schematically illustrated in FIG. 13. The sun gear 90 which is rotatably interlocked with the support member 30 and hence with the dose dial button 32 meshes with planetary gears 92. The receptacle 50 itself, in particular its circumferential wall serves as ring gear 80 and comprises a respective geared or toothed inner surface.

The support member 30 comprises axially extending fastening clips 94 that are adapted to provide an axial interlock of support member 30 and drive sleeve 26. The fastening clips 94 are adapted to match with a circumferential chamfer or notch 82 provided at the outside wall of the receptacle 50. In this way, the planetary gear 28 rotatably couples the support member 30 and the dose dial button 32 with the drive sleeve 26.

For setting of a dose and starting from a configuration as depicted in FIG. 2, the interlock member 34 is depressed, leading to a release of the latch mechanism 33. Consequently, the drive sleeve 26 is displaced in proximal direction by means of the spring element 24. Accordingly and due to the two-fold threaded engagement of the piston rod 22 with the housing 14 and with the drive sleeve 26, also the piston rod and its pressure piece 20 become subject to a respective proximal and rotational displacement. As the proximal stop position as illustrated in FIG. 3 has been reached, the dose dial button 32 at least partially protrudes from a proximal end face of the housing 14.

In this configuration, the dose dial button 32 is free to be rotated for setting of a pre-defined dose. A rotation of the dose dial button 32 is transferred to the drive sleeve 26 by means of the planetary gear 28. A respective gear transmission ratio is governed by the size and toothing of the meshing gears 90, 92, 80 of the planetary gear box. During dose setting or dose dialing, the dose button 32 and the drive sleeve 26 may remain axially fixed.

Since the piston rod 22 has been subject to a proximal displacement, an axial gap, which is not further illustrated, is formed between the pressure piece 20 and the piston 18 of the cartridge 16. By way of rotating the drive sleeve 26 while being in the proximal stop position as shown in FIG. 3, the piston rod 22 experiences a combined rotative and axially distally directed displacement. Consequently, the gap between the pressure piece 20 and the proximal end face of the piston 18 is reduced by a precisely defined magnitude.

In a subsequent dose dispensing procedure, the drive sleeve 26 is rotatably interlocked with respect to the housing 14 and experiences a distally directed displacement, e.g. by depressing of the dose dial button 32. During dose dispensing, the dose dial button 32 is displaced in distal direction until the distal stop position of dose dial button 32 and drive sleeve 26, as illustrated in FIG. 2, has been reached. Upon reaching said distal stop position, the pressure piece 20 abuts the proximal end face of piston 18 and pushes the piston 18 in distal direction by a predefined distance, which corresponds to the size of the previously set dose.

During subsequent dose dispensing procedures, the axial distance or forward movement of piston rod 22 and drive sleeve 26 is always constant. Various different doses can be set by varying the axial position of the piston rod 22 and the pressure piece 20 during a dose setting procedure prior to a dose dispensing action.

By means of the reduction gear 28 providing a rotational coupling of dose dial button 32 and drive sleeve 26, a rotative displacement of the drive sleeve 26 can be precisely tuned and a correspondingly precise axial displacement of the piston rod can be achieved.

In this way, even doses smaller than standard dose units can be set and dispensed, thus allowing to employ the drive mechanism and the respective dose dispensing device for paediatric applications.

The invention claimed is:

1. A drive mechanism for a drug delivery device, comprising:
   a housing;
   an axially displaceable piston rod to act on a piston of a cartridge containing a medicinal product to be dispensed;
   a drive member threadedly engaged with the piston rod and being slidably disposed and displaceable relative to the housing between a distal stop position and a proximal stop position, and comprising at its proximal end section a radially extending receptacle adapted to receive a reduction gear, where the reduction gear is exclusively operable to reduce the displacement of the drive member during dose setting and during dose dispensing the reduction gear is deactivated; and
   a dose dial member operably engaged with the drive member by means of the reduction gear, for transferring a dose setting rotative movement of the dose dial member at a lower rate of rotation to the drive member being rotatable with respect to the housing for setting of a dose.

2. The drive mechanism according to claim 1, wherein for dispensing of a dose, the drive member is slidably disposed relative to the housing from the proximal stop position to the distal stop position, and wherein the drive member is adapted to slave the piston rod in distal direction.

3. The drive mechanism according to claim 1, wherein the housing comprises a through opening for guiding of a distal portion of the piston rod.

4. The drive mechanism according to claim 3, wherein the through opening of the housing and the distal portion of the piston rod are correspondingly threaded.

5. The drive mechanism according to claim 1, wherein the drive member comprises a drive sleeve adapted to receive the piston rod at least partially and wherein the piston rod comprises a proximal portion with an outer proximal thread corresponding to an inner thread of the drive sleeve.

6. The drive mechanism according to claim 5 wherein threads on the distal and proximal portions of the piston rod and the are oppositely handed and comprise different leads.

7. The drive mechanism according to claim 1, wherein the threaded engagement of the piston rod and drive member is of non-self-locking type.

8. The drive mechanism according to claim 1, wherein the drive member is spring biased with respect to the housing in the axial direction.

9. The drive mechanism according to claim 1, wherein the drive member is locked in the distal stop position with respect to the housing by means of a latch mechanism.

10. The drive mechanism according to claim 1, wherein a proximally directed axial displacement of the drive member is delimited by a radially extending flange of the dose dial member adapted to abut with a radially inwardly directed flange of the housing.

11. The drive mechanism according to claim 1, wherein the receptacle that houses the reduction gear is closed in proximal direction by the dose dial member.

12. The drive mechanism according to claim 11, wherein the reduction gear comprises planetary gears meshing with a sun gear and with a surrounding ring gear, wherein the sun gear is rotatably locked with the dose dial member and the ring gear is rotatably locked with the drive member.

13. The drive mechanism according to claim 1, wherein the reduction gear comprises an epicyclic gear or a harmonic drive.

14. The drive mechanism according to claim 1, wherein upon the drive member reaching the proximal stop position, the dose dial member extends in proximal direction from a proximal end face of the housing.

15. The drive mechanism according to claim 1, wherein the dose dial member the reduction gear and/or the drive member are rigidly connected with each other in the axial direction.

16. The drive mechanism according to claim 1, wherein the dose dial member is axially connected with the drive member to displace the drive member in the distal direction in response to receive a distally directed injection force.

17. A dose dispensing device comprising the drive according to claim 1 and further comprising a cartridge filled with the medicinal fluid to be dispensed.

18. A drive mechanism for a drug delivery device, comprising:

a housing, an axially displaceable piston rod to act on a piston of a cartridge containing a medicinal product to be dispensed, a drive member threadedly engaged with the piston rod, where the drive member rotates about the threaded engagement with the piston rod during dose setting, a dose dial member operably engaged with the drive member by means of a reduction gear, wherein said reduction gear being exclusively operable to reduce the drive member's displacement during setting of a dose, and wherein the piston rod, the drive member, the dose dial member and/or the reduction gear are rotatably supported about a common or several axes of rotation being substantially co-aligned and the reduction gear is inoperable or deactivated during dispensing of a dose.

* * * * *